(12) United States Patent
Maliverney et al.

(10) Patent No.: US 9,102,780 B2
(45) Date of Patent: Aug. 11, 2015

(54) CATALYSTS FOR REACTION BETWEEN AN ISOCYANATE AND AN ALCOHOL

(75) Inventors: Christian Maliverney, Saint Julien su Bibost (FR); Laurent Saint-Jalmes, Vourles (FR)

(73) Assignee: BLUESTAR SILICONES FRANCE SAS, Lyons (FR)

( * ) Notice: Subject to any disclaimer, the term of this patent is extended or adjusted under 35 U.S.C. 154(b) by 299 days.

(21) Appl. No.: 13/123,981

(22) PCT Filed: Oct. 12, 2009

(86) PCT No.: PCT/EP2009/007309
§ 371 (c)(1),
(2), (4) Date: Jul. 11, 2011

(87) PCT Pub. No.: WO2010/043353
PCT Pub. Date: Apr. 22, 2010

(65) Prior Publication Data
US 2011/0263743 A1    Oct. 27, 2011

(30) Foreign Application Priority Data
Oct. 13, 2008   (FR) ..................... 08 05636

(51) Int. Cl.
| C08G 18/18 | (2006.01) |
| C08G 18/30 | (2006.01) |
| C08G 18/42 | (2006.01) |
| C07C 269/02 | (2006.01) |
| C08J 9/08 | (2006.01) |
| C08G 18/08 | (2006.01) |
| C08G 18/28 | (2006.01) |
| C08G 18/48 | (2006.01) |

(52) U.S. Cl.
CPC .......... *C08G 18/1816* (2013.01); *C07C 269/02* (2013.01); *C08G 18/14* (2013.01); *C08G 18/1808* (2013.01); *C08G 18/1858* (2013.01); *C08G 18/2815* (2013.01); *C08G 18/42* (2013.01); *C08G 18/4825* (2013.01); *C08J 9/08* (2013.01)

(58) Field of Classification Search
USPC ....................... 521/128, 129, 163; 528/52, 53

IPC ................ C07C 269/02; C08G 18/14,18/1808, C08G 18/1816, 18/1858, 18/2815, 18/42, C08G 18/4825; C08J 9/08
See application file for complete search history.

(56) References Cited

U.S. PATENT DOCUMENTS

| 3,645,924 | A | * | 2/1972 | Fogiel ........................... 521/129 |
| 4,025,466 | A | * | 5/1977 | Jourquin et al. .............. 521/115 |
| 4,192,925 | A | * | 3/1980 | Schafer et al. ................ 521/163 |
| 4,310,632 | A | * | 1/1982 | Horacek et al. ............... 521/121 |
| 4,328,330 | A | * | 5/1982 | Wellner et al. ................. 528/45 |
| 5,304,578 | A | * | 4/1994 | Tamano et al. ................ 521/51 |

\* cited by examiner

*Primary Examiner* — Rabon Sergent
(74) *Attorney, Agent, or Firm* — Dentons US LLP

(57) ABSTRACT

Processes are described for preparing polyurethane polymers by reacting an isocyanate with an alcohol using a non-tin based catalyst having the formula

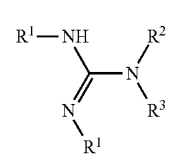
(1)

where $R^1$, which are identical or different, are a fluoroalkyl, monovalent alkyl, cycloalkyl, (cycloalkyl)alkyl, or the ring of the cycloalkyl group that optionally comprises at least one heteroatom, $R^2$ represents a hydrogen atom, an aromatic, arylalkyl, fluoroalkyl, alkylamine, alkylguanidine, monovalent alkyl, cycloalkyl or an alkyl group substituted by an optionally substituted ring, which optionally comprises at least one heteroatom, and $R^3$ represents an arylalkyl, fluoroalkyl, alkylamine, alkylguanidine, monovalent alkyl, cylcoalkyl, or alkyl group substituted by an optionally substituted ring which optionally comprises at least one heteroatom, when the $R^2$ radical is not a hydrogen atom, the $R^2$ and $R^3$ radicals optionally being linked to form a 3 to 7 membered optionally substituted aliphatic ring, and the $R^1$, $R^2$ and $R^3$ radicals do not comprise a silicon atom.

13 Claims, No Drawings

CATALYSTS FOR REACTION BETWEEN AN ISOCYANATE AND AN ALCOHOL

CROSS-REFERENCE TO PRIORITY/PCT APPLICATIONS

This application is the United States national phase of PCT/EP2009/007309, filed Oct. 12, 2009, and designating the United States (published in the French language on Apr. 22, 2010, as WO 2010/043353 A1; the title and abstract were also published in English), and claims priority of FR 0805636, filed Oct. 13, 2008, each hereby expressly incorporated by reference in its entirety and each assigned to the assignee hereof.

The invention relates to novel catalysts for the reaction between an isocyanate and an alcohol, which is a key stage in the preparation of polyurethane polymers. It relates more specifically to the use of novel catalysts which are not based on tin.

Polyurethanes were initially used in the manufacture of plastic compounds and foams. These polymers have since been developed in very diverse fields of application, such as elastomers, thermoplastics, thermosetting resins, expanded systems, textile fibers and coating systems (coating slips for paper, wood coatings, motor vehicle paints, adhesives, and the like).

Polyurethanes are polymers which comprise at least one urethane group (also known as carbamate group). This group results from the reaction between an alcohol group and an isocyanate group.

Generally, the synthesis of a polyurethane by an uncatalyzed reaction of an isocyanate with a primary or secondary alcohol is carried out at between 50 and 100° C. Numerous catalysts have already been proposed to thus optimize this reaction, for example Lewis acids and bases, and also numerous metal salts. Examples of these catalysts are described in the following papers:

Gambiroza-Jukic et al., Kinetic analysis of bulk polymerization of diisocyanate and polyol; J. Appl. Polym. Sci., 1993, vol. 47, pp. 513-519, Wong et al., Catalysis in competing isocyanate reactions, competing phenyl isocyanate reaction catalyzed with N,N,N',N'',N''-pentamethyldipropylene-triamine; J. Polym. Sci.; Part A, Polym. Chem. Ed., 1986, vol. 24, pp. 2877-2890, and Okada, H. et al., The kinetics of the polyurethane-forming reaction between organic diisocyanates and glycols; Makromol. Chem., 1963, vol. 66, pp. 91-101.

The most widely used metal catalysts are alkyltin carboxylates, the best known of which is dibutyltin dilaurate. However, catalysts based on alkyltin, although very efficient, exhibit the disadvantage of being toxic (CMR-2: toxic for reproduction).

Consequently, a search is underway to replace them in numerous applications with compounds not exhibiting these disadvantages. In addition, the industry is always on the lookout for compounds which are at least as active as dibutyltin dilaurate but which are not based on tin.

The essential objective of the present invention is thus to provide a catalyst for the reaction between an isocyanate and an alcohol which is at least as active as dibutyltin dilaurate but which is not based on tin.

Another essential objective of the present invention is to provide a catalyst which can be used in the synthesis of polyurethanes.

There has now been found, and it is this which constitutes the subject-matter of the present invention, a novel process for preparing a compound A having at least one urethane functional group, comprising a stage 1) which consists in reacting a compound B, having at least one isocyanate functional group, with a compound D, having at least one hydroxyl functional group, in the presence of a catalyst C, characterized in that said catalyst C is different from the compound D and is a non-silyl organic compound corresponding to the general formula (1):

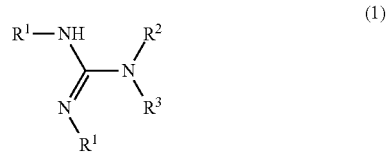

in which:
the $R^1$ radicals, which are identical or different, represent, independently of one another, a linear or branched monovalent alkyl group, a cycloalkyl group, a (cycloalkyl)alkyl group, the ring being substituted or unsubstituted and being able to comprise at least one heteroatom, or a fluoroalkyl group, the $R^2$ radical represents a hydrogen atom, a linear or branched monovalent alkyl group, a cycloalkyl group, an alkyl group substituted by a ring, which is substituted or unsubstituted and which can comprise at least one heteroatom, an aromatic group, an arylalkyl group, a fluoroalkyl group or an alkylamine or alkylguanidine group, and the $R^3$ radical represents a linear or branched monovalent alkyl group, a cylcoalkyl group, an alkyl group substituted by a ring, which is substituted or unsubstituted and which can comprise at least one heteroatom, or an arylalkyl, fluoroalkyl, alkylamine or alkylguanidine group, when the $R^2$ radical is not a hydrogen atom, the $R^2$ and $R^3$ radicals can be linked up to form a 3-, 4-, 5-, 6- or 7-membered aliphatic ring optionally substituted by one or more substituents, and with the additional condition that the $R^1$, $R^2$ and $R^3$ radicals do not comprise a silicon atom.

In order to achieve this objective, the inventors have had the credit of demonstrating, entirely surprisingly and unexpectedly, that the use of a non-silyl compound corresponding to the general formula (I) makes it possible to catalyze the reaction between an isocyanate and an alcohol, which is a key stage in the preparation of polyurethane polymers.

The non-silyl compounds according to the invention corresponding to the general formula (1) are 1,2,3-trisubstituted and 1,2,3,3-tetrasubstituted guanidines and exhibit the advantage of being liquid, colorless and odorless.

It should be noted that at least a part of the inventive nature of the invention is due to the judicious and advantageous selection of the delimited combinations of compounds C according to the invention used as catalyst.

According to a preferred embodiment of the invention, the catalyst C is a non-silyl organic compound corresponding to the general formula (1) described above and in which:

the $R^1$ radicals, which are identical or different, and the $R^3$ radical are chosen, independently of one another, from the group consisting of: an isopropyl radical, a cyclohexyl radical and a linear or branched monovalent $C_1$-$C_{12}$ alkyl radical, the $R^2$ radical represents a hydrogen atom, a linear or branched monovalent alkyl group, a cycloalkyl, group, an alkyl group substituted by a ring, which is substituted or unsubstituted and which can comprise at least one heteroatom, an arylalkyl group, a fluoroalkyl group or an alkylamine or alkylguanidine group, and when the $R^2$ radical is not a hydrogen atom, the $R^2$ and $R^3$ radicals can be linked up to form a 3-, 4-, 5-, 6- or 7-membered aliphatic ring optionally substituted by one or more substituents.

According to another preferred embodiment, the catalyst C is a non-silyl organic compound chosen from the group consisting of the following compounds (A1) to (A6):

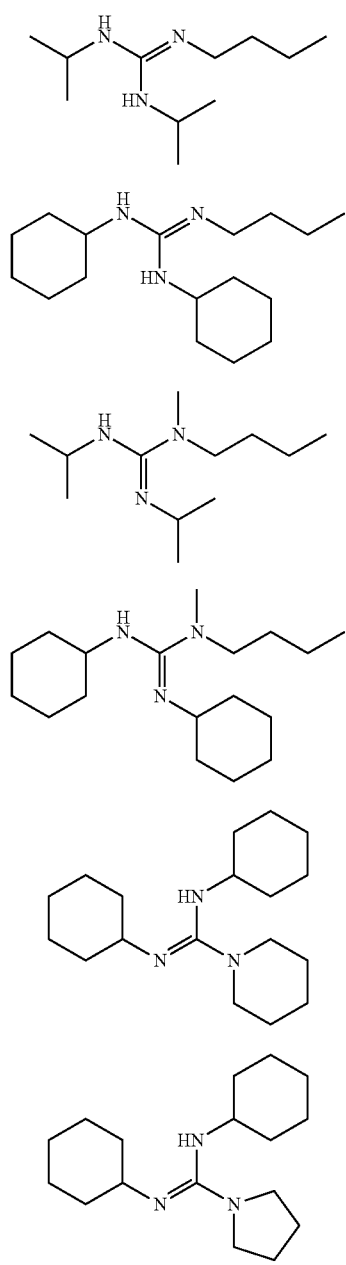

The amount of catalyst is advantageously determined so that the amount is between 0.001 and 0.1% by weight, with respect to the total amount of the reaction mixture, and preferably between 0.005 and 0.5% by weight, with respect to the total weight of the reaction mixture.

According to another preferred embodiment, the process according to the invention is particularly suitable for the preparation of polyurethane polymers. Thus, according to a preferred alternative form of the invention, the compound A having at least one urethane functional group is a polyurethane, the compound B having at least one isocyanate functional group is a diisocyanate and the compound D having at least one hydroxyl functional group is a polyol.

According to another preferred embodiment, the process according to the invention is characterized in that stage 1) consists in reacting, in the absence of moisture and in the presence of an effective amount of the catalyst C according to the invention and as described above, at least one compound B, which is an isocyanate chosen from the group consisting of monoisocyanates, diisocyanates, polyisocyanates and their mixtures, and at least one compound D, which is an alcohol chosen from the group consisting of monoalcohols, diols, polyols and their mixtures.

Mention may be made, by way of illustration of compounds B of use according to the invention and having at least one isocyanate functional group, of mono-, di- or polyisocyanates which are aromatic, cyclic, saturated or aliphatic and which are well known to a person skilled in the art, and the mixtures of these compounds.

According to the standard use in chemistry, when a functional group has given its name to a family of compounds (in other words, when a functional group is eponymous with a family of products, as is the case for the isocyanates), the aromatic or aliphatic nature is defined according to the point of attachment of the functional group under consideration.

When an isocyanate is situated on a carbon of aliphatic nature, then it is considered that the isocyanate compound is itself of aliphatic nature. Likewise, when an isocyanate functional group is attached to the backbone via a carbon of aromatic nature, then the whole of the monomer will be denoted by the expression aromatic isocyanate. Thus:

any isocyanate functional group for which the point of attachment of the nitrogen is a member of an aromatic ring is regarded as "aromatic"; and any isocyanate functional group for which the point of attachment of the nitrogen is a carbon of $sp^3$ hybridization is regarded as "aliphatic".

Mention may be made, as examples of aromatic isocyanates, of diphenylmethane diisocyanate (MDI), in particular 4,4'-diphenylmethane diisocyanate or 2,4'-diphenylmethane diisocyanate, or toluene diisocyanate (TDI), in particular 2,4-toluene diisocyanate and 2,6-toluene diisocyanate.

Mention may be made, as examples of aliphatic isocyanates, of hexamethylene diisocyanate (HMDI), 1,3-tetramethylxylylene diisocyanate, isophorone diisocyanate and dicyclohexamethylmethane diisocyanate.

Mention may be made, as examples of cycloaliphatic diisocyanates, of isophorone diisocyanate (IPDI).

It is thus possible, for the preparation of a linear polyurethane polymer, to conventionally react a diisocyanate and a diol. The reactions concerned can progress according to numerous alternative forms: at least two reactants of different types (isocyanate/alcohol) have to be involved; these reactants can be mono- or difunctional.

Mention may be made, as example of compound D having at least one hydroxyl functional group, without intending to be restricted thereto, of polyols, such as glycerol, polyglycerol, glycol, propylene glycol, glycols comprising from 2 to 10 carbon atoms, preferably from 2 to 6 carbon atoms, such as ethylene glycol, diethylene glycol, 1,4-butanediol, 1,5-pentanediol, 1,6-hexane-diol, 1,10-decanediol, 1,3-propanediol, dipropylene glycol, polyethylene glycol, polypropylene glycol, neopentyl glycol, pentaerythritol, neopentyl glycol hydroxypivalate, dipentaerythritol, trimethylolpropane, 2-butyl-2-ethyl-1,3-propanediol, sorbitol, mannitol, xylitol and meso-erythritol. Use may also be made of esters of these diols or polyester polyols and also polyether polyols.

In a known way, the polyester polyols are generally chosen from aliphatic and aromatic polyester polyols and the mixtures of these compounds.

Mention may be made, by way of example, of the polyester polyols resulting from the condensation of aliphatic, cyclic or aromatic polyols, such as 1,2-ethanediol, 1,2-propanediol, 1,3-propanediol, glycerol, trimethylolpropane, 1,6-hexanediol, 1,2,6-hexanetriol, butenediol, sucrose, glucose, sorbitol, pentaerythritol, mannitol, triethanolamine, N-methyldiethanolamine and the mixtures of these compounds, with a dicarboxylic acid, such as 1,6-hexanedioic acid, dodecanedioic acid, azelaic acid, sebacic acid, adipic acid, 1,18-octadecanedioic acid, phthalic acid, succinic acid and the mixtures of these diacids, an unsaturated anhydride, such as maleic anhydride or phthalic anhydride, or a homopolymer of a lactone, such as ε-caprolactone.

The polyester polyols are generally obtained by the use of an excess of di- or polyfunctional alcohol in their polyesterification with dicarboxylic acids or carboxylic acid anhydrides.

The polyether polyols are generally obtained by the anionic or cationic polyaddition of cyclic monomers, such as ethylene oxide, propylene oxide or tetrahydrofuran.

The molar masses of the polyether polyols used in the synthesis of polyurethanes generally vary from 250 to 8000. Their functionality can range from 2 to 7, depending on the nature of the molecule used as initiator. The end groups of these polyether diols can be primary or secondary.

According to another preferred embodiment, the process according to the invention is characterized in that stage 1) is carried out in the presence of an expanding agent.

Numerous expanding agents are well known in the art and they are used in amounts varied according to the cell size desired in the final product, which is a polyurethane foam. The most economic of these agents is water but use is often made, alone or mixed with water, of halogenated short-chain alkanes carrying chlorine and/or fluorine. The expanding agents are often used in amounts amounting to up to 50% of the weight of the polyol.

Of course, various modifications may be introduced by a person skilled in the art into the processes which have just been described solely by way of nonlimiting examples without departing from the scope of the invention.

Other advantages and characteristics of the present invention will become apparent on reading the following examples, given by way of illustration and without implied limitation.

EXAMPLES

1) Preparation of the Catalysts According to the Invention a) 1-Butyl-2,3-diisopropylguanidine (A1)

Reaction Scheme

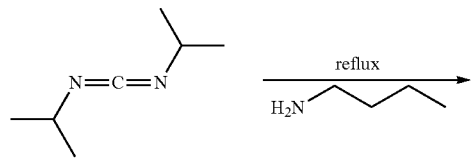

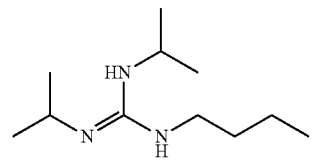

A mixture of 33 g of N-butylamine (0.45 mol) and 19 g of diisopropylcarbodiimide (0.15 mol) is heated at reflux for 3 h 30. The analysis by GC then shows a conversion of the diisopropylcarbodiimide of greater than 99.5%. The colorless final mixture is concentrated at 60° C. under 20 mbar for 2 h to give 29 g of a colorless and virtually odorless liquid of low viscosity, corresponding to the expected guanidine (yield 96.7%).

$^1$H NMR/CDCl$_3$ (ppm): 0.93 (3H, t), 1.14 (12H, d), 1.37 (2H, sex), 1.52 (2H, quint), 3.01 (2H, t), 3.57 (2H, m).

b) 1-Butyl-2,3-diisopropyl-1-methylguanidine (A2)

Reaction Scheme

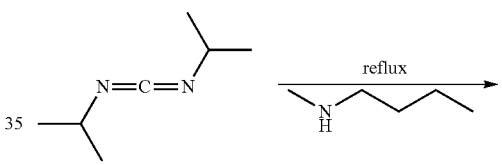

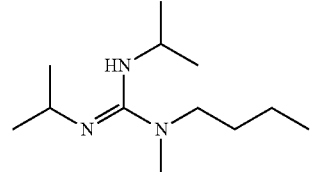

A mixture of 32.68 g of N-butyl-N-methylamine (0.375 mol) and 23.66 g of diisopropylcarbodiimide (0.1875 mol) is heated at reflux for 3 h. The analysis by GC then shows a conversion of the diisopropylcarbodiimide of greater than 99.5%. The colorless final mixture is concentrated at 60° C. under 5 mbar for 2 h to give 40 g of a colorless and virtually odorless liquid of low viscosity, corresponding to the expected guanidine (yield 100%).

¹H NMR/CDCl₃ (ppm): 0.88 (3H, t), 1.06 (12H, d), 1.26 (2H, sex), 1.46 (2H, quint), 2.67 (3H, s), 3.05 (2H, t), 3.35 (2H, m).

c) 1-Butyl-2,3-dicyclohexylguanidine (A3) CAS RN=60006-40-8

Reaction Scheme

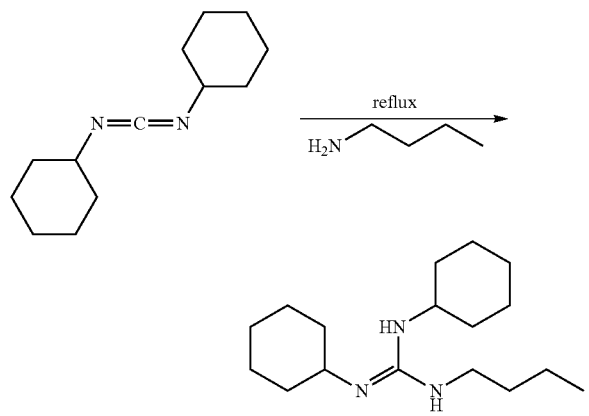

A mixture of 15.69 g of N-butylamine (0.214 mol) and 22.13 g of dicyclohexylcarbodiimide (0.107 mol) is heated at reflux for 2 h. The analysis by GC then shows a conversion of the dicyclohexylcarbodiimide of greater than 99.6%. The colorless final mixture is concentrated at 60° C. under 1 mbar for 2 h to give 29.7 g of a colorless and virtually odorless liquid of moderate viscosity corresponding to the expected guanidine (yield 99%).

d) 1-Butyl-2,3-dicyclohexyl-1-methylguanidine (A4)

Reaction Scheme

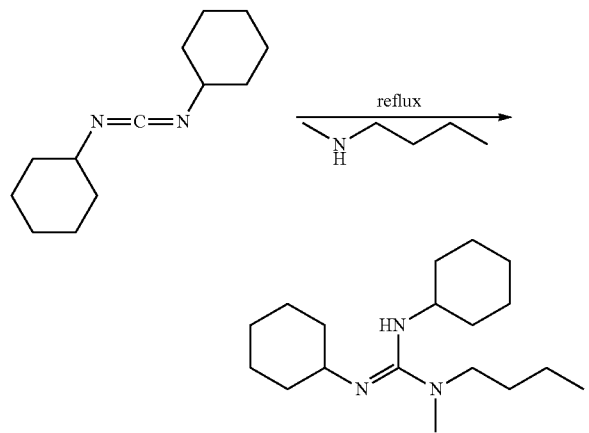

A mixture of 17.78 g of N-butyl-N-methylamine (0.204 mol) and 21.05 g of dicyclohexylcarbodiimide (0.102 mol) is heated at reflux for 3 h. The analysis by GC then shows a conversion of the dicyclohexylcarbodiimide of greater than 99.5%. The colorless final mixture is concentrated at 60° C. under 1 mbar for 2 h to give 29.9 g of a colorless and virtually odorless liquid of moderate viscosity corresponding to the expected guanidine (yield 99.7%).

¹H NMR/CDCl₃ (ppm): 0.89 (3H, t), 1-1.4 (10H, m), 1.47 (2H, quint), 1.5-2 (12H, several m), 2.67 (3H, s), 2.90 (1H, m), 2.97 (1H, m), 3.06 (2H, t).

e) 1,2-Dicyclohexyl-3-piperidylguanidine (A5) CAS RN 60006-25-9

Reaction Scheme

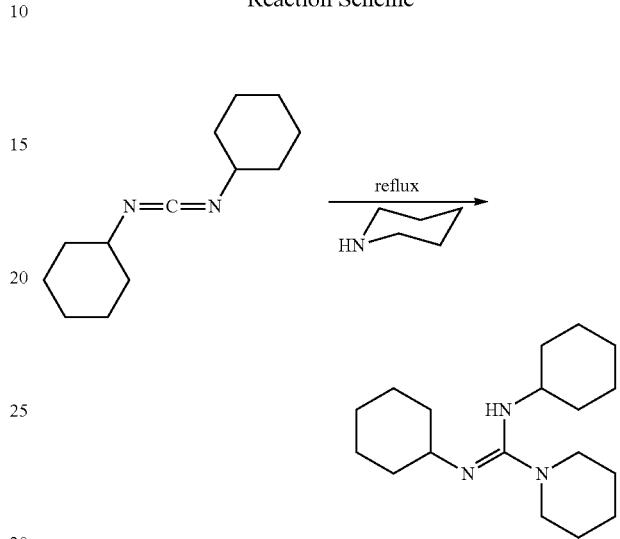

A mixture of 11.69 g of piperidine (0.137 mol) and 14.16 g of dicyclohexylcarbodiimide (0.0686 mol) is heated at reflux for 3 h 30. The analysis by GC then shows a conversion of the dicyclohexylcarbodiimide of greater than 99.7%. The colorless final mixture is concentrated at 60° C. under 1 mbar for 2 h to give 19.9 g of a colorless and virtually odorless liquid of high viscosity corresponding to the expected guanidine (yield 99.5%).

f) 1,2-Dicyclohexyl-3-pyrrolidylguanidine (A6) CAS RN 60006-28-2

Reaction Scheme

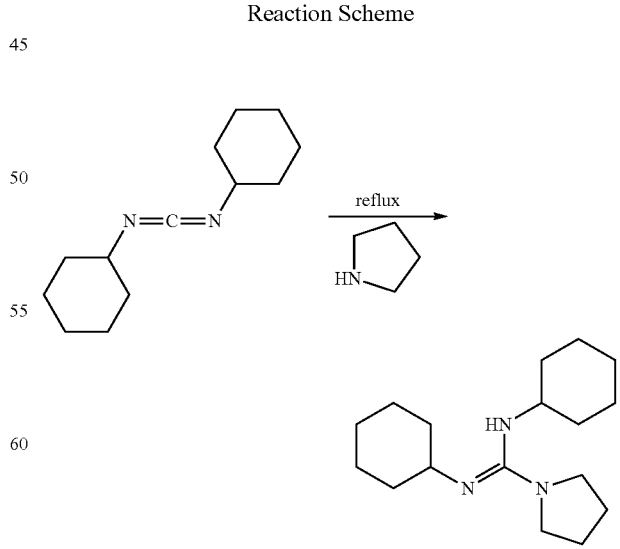

A mixture of 19.2 g of pyrrolidine (0.27 mol) and 18.6 g of dicyclohexylcarbodiimide (0.09 mol) is heated at reflux for 4 h. The analysis by GC then shows a conversion of the dicyclohexylcarbodiimide of greater than 99.8%. The colorless final mixture is concentrated at 60° C. under 1 mbar for 1 h to give 24.9 g of a colorless and virtually odorless liquid of moderate viscosity corresponding to the expected guanidine (yield 99.6%).

2) Operating Conditions

A formulation composed of 2,4-TDI (2,4-diisocyanato-1-methylbenzene) and of polypropylene glycol with a weight of 2000 g/mol is prepared with an OH/NCO molar ratio which is equal to 0.5. The catalyst is added to this formulation. The tests are carried out in a jacketed reactor at 60° C. under a nitrogen headspace.

In order to be able to establish comparisons with the comparative catalyst (tin catalyst, dibutyltin dilaurate or DBTL), the catalysts (A2) and (A4) and the comparative (DBTL) are employed by addition of 0.01% by weight, with respect to the total weight of the mixture.

Kinetic monitoring is carried out by quantitatively determining the —N=C=O (NCO) functional groups in the usual way, according to the standard AFNOR NF T 52-132 (September 1988), sometimes denoted by dibutylamine method. The principle of this quantitative determination is based on the reaction of the isocyanate groups with the excess di(n-butyl)amine. The amine is introduced in solution in toluene (1N). The reaction time is 15 minutes at ambient temperature. The excess di(n-butyl)amine is subsequently quantitatively determined by titration with hydrochloric acid (1N). Bromocresol green is used as indicator.

It is observed that:
a) a degree of conversion of the isocyanate functional groups of 20% is achieved after:
  a few minutes for the DBTL (comparative), and
  50 min and 55 min for the catalysts (A2) and (A4) respectively;
b) a degree of conversion of the isocyanate functional groups of 50% is achieved after:
  10 min for the DBTL (comparative), and
  180 min and 205 min for the catalysts (A2) and (A4) respectively.

It should be noted that the delay in the reaction with the catalysts (A2) and (A4), with respect to the comparative, is advantageous as, in some applications, a latent period for the crosslinking is desired.

The molecular weight distribution obtained and the use of twofold detection in gel permeation chromatography or GPC (refractometer (RI) and UV) make it possible to affirm the effectiveness of the catalysts (A2) and (A4) according to the invention.

This result is satisfactory and shows the viability of a tin-free catalyst according to the invention. Furthermore, as the kinetics of formation of the polyurethane polymer are slightly slower with the catalyst according to the invention, this exhibits the advantage of giving more time for a stage of forming the polyurethane polymer.

What is claimed is:

1. A process for preparing a compound A having at least one urethane functional group, the process comprising a stage 1) which comprises reacting a compound B, having at least one isocyanate functional group, with a compound D, having at least one hydroxyl functional group, in the presence of a catalyst C, wherein the catalyst C is a compound of the formula:

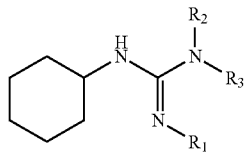

in which:

the $R^1$ radical represents a linear or branched monovalent alkyl group, a cycloalkyl group, or a (cycloalkyl)alkyl group, cycloalkyl being substituted or unsubstituted and optionally comprising at least one heteroatom, or a fluoroalkyl group the $R^2$ radical represents a hydrogen atom, a linear or branched monovalent alkyl group, a cycloalkyl group, an alkyl group substituted by a ring, which is substituted or unsubstituted and which optionally comprise at least one heteroatom, an aromatic group, an arylalkyl group, a fluoroalkyl group, or an alkylamine or an alkylguanidine group, and the $R^3$ radical represents a linear or branched monovalent alkyl group, a cylcoalkyl group, an alkyl group substituted by a ring, which is substituted or unsubstituted and which optionally comprise at least one heteroatom, or an arylalkyl group, a fluoroalkyl group, an alkylamine group, an alkylguanidine group, when the $R^2$ radical is not a hydrogen atom, the $R^2$ and $R^3$ radicals are optionally linked to form a 3-, 4-, 5-, 6- or 7-membered aliphatic ring optionally substituted by one or more substituents, and wherein the $R^1$, $R^2$ and $R^3$ radicals do not comprise a silicon atom.

2. The process as claimed in claim 1, wherein the catalyst C is a non-silyl organic compound corresponding to formula (1) where:

the $R^1$ radical and the $R^3$ radical are selected, independently of one another, from the group consisting of: an isopropyl radical, a cyclohexyl radical and a linear or branched monovalent $C_1$-$C_{12}$ alkyl radical, the $R^2$ radical represents a hydrogen atom, a linear or branched monovalent alkyl group, a cycloalkyl group, an alkyl group substituted by a ring, which is substituted or unsubstituted and which optionally comprise at least one heteroatom, an arylalkyl group, a fluoroalkyl group or an alkylamine or alkylguanidine group, and when the $R^2$ radical is not a hydrogen atom, the $R^2$ and $R^3$ radicals optionally being linked to form a 3-, 4-, 5-, 6- or 7-membered aliphatic ring optionally substituted by one or more substituents.

3. A process for preparing a compound A having at least one urethane functional group, the process comprising a stage 1) which comprises reacting a compound B, having at least one isocyanate functional group, with a compound D, having at least one hydroxyl functional group, in the presence of a catalyst C, wherein the catalyst C is selected from the group consisting of compounds (A3), (A4), (A5) and (A6):

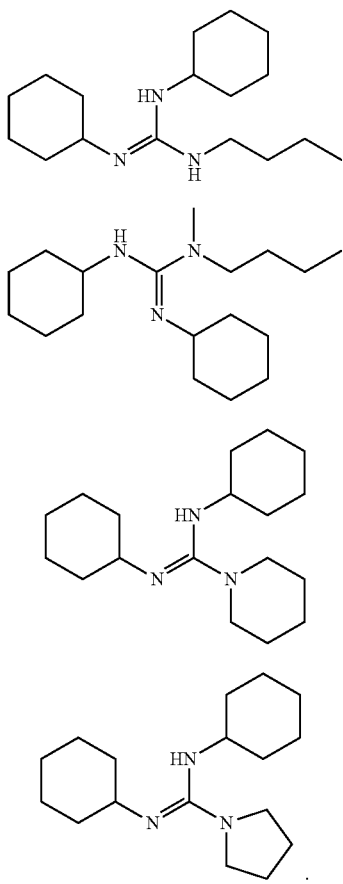

wherein compounds (A3), (A4), (A5) and (A6) are 1-butyl-2,3-dicyclohexylguanidine, 1-butyl-2,3-dicyclohexyl-1-methylguanidine, 1,2-dicyclohexyl-3-piperidylguanidine and 1,2-dicyclohexyl-3-pyrrolidylguanidine, respectively.

4. The process as claimed in claim 1, wherein compound A is a polyurethane, compound B is a diisocyanate and compound is a polyol.

5. The process as claimed in claim 1, wherein stage 1) comprises reacting, without moisture and with a catalytically effective amount of the catalyst C being present, at least one compound B, which is an isocyanate selected from the group consisting of a monoisocyanate, a diisocyanate, a polyisocyanate and theft mixtures, and at least one compound D, which is an alcohol selected from the group consisting of a monoalcohol, a diol, a polyol and their mixtures.

6. The process as claimed in claim 1, wherein compound B is a diisocyanate selected from the group consisting of: diphenylmethane diisocyanate (MDI), toluene diisocyanate (TDI), hexamethylene diisocyanate (HMDI), 1,3-tetramethylxylylene diisocyanate, isophorone diisocyanate, dicyclohexamethylmethane diisocyanate and isophorone diisocyanate (IPDI).

7. The process as claimed in claim 4, wherein compound D is a polyester polyol.

8. The process as claimed in claim 1, wherein stage 1) is carried out with an expanding agent being present.

9. The process as claimed in claim 6, wherein the diphenylmethane diisocyanate (MDI) is 4,4'-diphenylmethane diisocyanate or 2,4'-diphenylmethane diisocyanate.

10. The process as claimed in claim 6, wherein the toluene diisocyanate (TDI) is 2,4-toluene diisocyanate or 2,6-toluene diisocyanate.

11. The process as claimed in claim 8, wherein the expanding agent is water.

12. The process as claimed in claim 1, wherein, in formula (I), the $R^1$ radical is cyclohexyl or n-butyl, $R^2$ is hydrogen or methyl and $R^3$ is cyclohexyl or n-butyl, or $R^2$ and $R^3$ are combined with the adjacent nitrogen atom to form a piperidine or pyrrolidine ring.

13. The process as claimed in claim 3, wherein the catalyst C is 1-butyl-2,3-dicyclohexyl-1-methylguanidine or 1-butyl-2,3-dicyclohexylguanidine.

* * * * *